United States Patent [19]

de Jong

[11] 4,247,723

[45] Jan. 27, 1981

[54] PREPARATION OF DIHYDROMYRCENOL

[75] Inventor: Aaldert J. de Jong, Amsterdam, Netherlands

[73] Assignee: Shell Oil Company, Houston, Tex.

[21] Appl. No.: 761,082

[22] Filed: Jan. 21, 1977

[30] Foreign Application Priority Data

Feb. 4, 1976 [GB] United Kingdom ............... 4371/76

[51] Int. Cl.$^2$ ............................................. C07C 29/00
[52] U.S. Cl. .................................. 568/875; 585/601; 560/247
[58] Field of Search ............... 260/631.5, 489, 680 C; 568/875, 877; 585/601; 560/247

[56] References Cited

U.S. PATENT DOCUMENTS

| | | | |
|---|---|---|---|
| 2,871,271 | 1/1959 | Booth | 260/631.5 |
| 2,902,510 | 9/1959 | Webb | 260/489 |
| 3,418,386 | 12/1968 | Hays | 260/666 |
| 3,487,118 | 12/1969 | Blumenthal | 260/631.5 |
| 3,622,646 | 11/1971 | Wolford et al. | 260/680 C |

OTHER PUBLICATIONS

Akulogawa et al., Chem. Abst., vol. 80, #3058h, (1974).
Suga et al., Chem. Abst., vol. 77, #5029R, (1972).

*Primary Examiner*—Norman Morgenstern
*Assistant Examiner*—James H. Reamer

[57] ABSTRACT

Dihydromyrcenol (3,7-dimethylocta-1-en-7-ol) and carboxylic acid esters thereof are prepared from dimethylcyclooctene reactant mixtures comprising 1,5-dimethylcyclooctene in admixture with 1,6-dimethylcyclooctene and/or 1,4-dimethylcyclooctene by (a) thermally isomerizing the dimethylcyclooctene reactant mixture to afford a mixed octadiene product comprising 2,6-dimethylocta-1,7-diene in admixture with 2,7-and/or 2,5-dimethylocta-1,7-diene, (b) reacting the mixed octadiene product with a carboxylic acid to selectively form the ester of 3,7-dimethyl-octa-1-en-7-ol and (c) optionally hydrolyzing the ester of 3,7-dimethyl-octa-1-en-7-ol under basic conditions to yield dihydromyrcenol.

6 Claims, No Drawings

PREPARATION OF DIHYDROMYRCENOL

BACKGROUND OF THE INVENTION

This invention relates to a process for the preparation of 3,7-dimethylocta-1-en-7-ol (dihydromyrcenol) or carboxylic esters thereof.

Dihydromyrcenol is a well known aroma chemical; its properties and preparation by the reduction of myrcenol having been described previously in U.S. Pat. No. 2,871,271. It is also known from U.S. Pat. Nos. 2,902,510 and 3,487,118 that dihydromyrcenol can be prepared from 2,6-dimethylocta-2,7-diene (dihydromyrcene) by carboxylic acid ester formation and subsequent hydrolysis. While both of these previously developed preparative techniques can be employed in the synthesis of dihydromyrcenol, their usefulness is somewhat limited by the fact that they both employ turpentine derivatives (myrcenol and dihydromyrcene) as starting materials.

In contrast, the present invention is concerned with a procedure for preparing dihydromyrcenol and its carboxylic acid esters in good yield from alternative starting materials which are readily obtained from industrial sources.

SUMMARY OF THE INVENTION

It has now been found that dihydromyrcenol and carboxylic acid esters thereof can be selectively prepared from a mixture of dimethylcyclooctene isomers made up of 1,5-dimethylcyclooctene in admixture of 1,6-dimethylcyclooctene and/or 1,4-dimethylcyclooctene by the process steps comprising:

(a) thermally isomerizing the isomer mixture to afford a mixed open-chain octadiene product comprising 2,6-dimethylocta-1,7-diene in admixture with 2,7-and/or 2,5-dimethylocta-1,7-diene, (b) contacting the mixed octadiene product with a carboxylic acid whereby the 2,6-dimethylocta-1,7-diene selectively reacts to form an ester of 3,7-dimethylocta-1-en-7-ol and (c) optionally hydrolyzing the ester of 3,7-dimethylocta-1-en-7-ol thus formed under basic conditions to yield dihydromyrcenol.

Dihydromyrcenol preparation according to the invention is of advantage in that it utilizes a mixed dimethylcyclooctene starting material available from synthetic sources i.e., dimerized isoprene which has been selectively hydrogenated in accordance with known techniques. The use of this mixed dimethylcyclooctene starting material without difficult isomer separation is made possible by the discovery of the heretofore unknown selective nature of the ester forming reaction which is employed in the synthesis process. That is, it has surprisingly been found that when the mixture of open-chain dienes from step (b) of the process is reacted with a carboxylic acid, only the desired ester of dihydromyrcenol is formed via addition of the acid to the 2,6-dimethylocta-1,7-diene. Other isomeric dienes are apparently unreactive.

DESCRIPTION OF THE PREFERRED EMBODIMENTS

The isomeric dimethylcyclooctene reactant mixtures employed as starting materials in the process according to the invention are suitably derived from isoprene using synthetic techniques which are known in the art. A preferred starting material may be obtained by the selective hydrogenation of a mixture of 1,5-and 1,6-dimethylcycloocta-1,5-diene in the presence of a noble metal catalyst according to the technique described by Suga et al in Israel Journal of Chemistry, 10,15-18 (1972). This cyclooctadiene mixture is readily formed by the catalytic dimerization of isoprene which is also described in Suga et al, the catalyst being, for example, a nickel (0) phosphite complex. The mixture preferably contains at least 50% w of the 1,5-isomer. The mixture may be hydrogenated selectively in the presence of a palladium catalyst optionally supported on a carrier such as charcoal. The hydrogenation may be carried out at atmospheric pressure or above and the temperature is preferably from 20° to 100° C.

The dimethylcyclooctene starting material for the process of the invention which is obtained from the selective hydrogenation of such a mixture of cyclooctadiene derivatives contains 1,5-dimethylcyclooctene derived from the 1,5-dimethylcycloocta-1,5-diene together with 1,4- and/or 1,6-dimethylcyclooctene derived from the 1,6-dimethylcycloocta-1,5-diene. When the dimethylcyclooctenes are thermally isomerized, for example, by heating to 500° to 550° C., they are converted to open-chain dimethyloctadienes. Thus, 1,5-dimethylcyclooctene is converted to 2,6-dimethylocta-1,7-diene while 1,4- and 1,6-dimethylcyclooctene are converted to 2,5- and 2,7-dimethylocta-1,7-diene, respectively. This thermal isomerization step is also conventional with further details being given, for example, in the above mentioned Suga et al article at page 17. Typically, the isomerization reaction is carried out by passing the dimethylcyclooctene starting material, optionally preheated, through a tubular reaction zone maintained at the desired reaction temperature. Optionally, the starting material may be diluted with an inert carrier gas such as nitrogen. The residence time for thermal isomerization is generally quite short, e.g., 0.5 to 5 minutes.

In step (b) of the process, the dimethyloctadiene product is reacted with a carboxylic acid, preferably of up to 4 carbon atoms, for example, formic, acetic and propionic acids with formic acid being most preferred. It is surprisingly found that when a mixture of dimethyloctadienes is used, only 2,6-dimethylocta-1,7-diene appears to react with the carboxylic acid to form an ester. The ester obtained is the desired ester of 3,7-dimethylocta-1-en-7-ol formed by addition of the acid across the

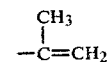

grouping. The reaction with the carboxylic acid may in some cases be carried out in the presence of a strong acid catalyst, for example sulfuric acid. However, in other cases where highly acidic acids such as formic acid is used, the acid catalyst does not appear to be necessary for the ester forming reaction. The temperature of the reaction is preferably from 0° to 60° C., for example, 15° to 30° C. Reaction times vary with the temperature employed, but are generally from 3 to 24 hours.

The optional hydrolysis of the ester under basic conditions may be carried out using conventional procedures, for example, by reacting the ester with an alkali metal hydroxide such as sodium hydroxide in an aqueous alkanol, for example aqueous methanol.

It will be appreciated from the above that the process of the invention offers a convenient route to dihydromyrcenol and its esters in particular when the starting material is an isomer mixture. In this case, no involved isomer separation is necessary in the process since the desired product can be readily separated from the reaction mixture after ester formation and optional hydrolysis by known techniques, e.g., distillation, taking into account known differences in the physical and chemical properties of the reacted versus unreacted octadiene intermediates.

The invention is illustrated further in the following Example.

EXAMPLE

Preparation of starting material 100 g of a mixture containg 85% w 1,5-dimethylcyclocta-1,5-diene and 15% w 1,6-dimethylcycloocta-1,5-diene in n-heptane (100 ml) was stirred with 10% palladium on charcoal (3.0 g) for 7 hours at 100° C. under a hydrogen atmosphere (1 bar). The product was shown by GLC to contain a mixture of dimethylcyclooctenes and less than 5% w of fully saturated compounds.

(a) Thermal isomerization

The mixture of dimethylcyclooctenes prepared above was passed at a rate of 60 ml per hour, together with nitrogen at a rate of 5 l per hour, through a quartz tube (300 mm×20 mm diam) heated at 510° C. The conversion of starting material was 61%. The crude product was distilled under reduced pressure to give a diene mixture boiling at 88°–96° C. at 100 mm Hg and consisting of 75% w 2,6-dimethylocta-1,7-diene and 25% w of isomeric open-chain dienes.

(b) Esterification 17 g of the diene mixture obtained in (b) was stirred for 5 hours at 20° C. with formic acid (34 g). The mixture was then analyzed by Gas Liquid Chromatography and shown to contain, as the only ester present, the formate ester of 3,7-dimethylocta-1-en-7-ol derived from the 2,6-dimethylocta-1,7-diene. The mixture was mixed with water (100 ml) and extracted with n-pentane (2×100 ml). The extracts were washed with water and dried and solvent was removed under reduced pressure to yield 18 g of the crude ester.

(C) Hydrolysis

The crude ester from (b) was heated under reflux with sodium hydroxide (3.0 g), water (20 ml) and methanol (100 ml) for 1.5 hours. Most of the methanol was then removed under reduced pressure and a further 100 ml of water was added to the mixture which was then extracted with cyclohexane (2×75 ml). The extracts were washed with water and dried (MgSO$_4$). The cyclohexane, together with the unreacted open-chain dienes, was then removed under reduced pressure and the residue was distilled to give 3,7-dimethylocta-1-en-7-ol (8.9 g, b.p. 111° C. at 50 mm Hg).

What is claimed is:

1. A process for the preparation of 3,7-dimethylocta-1-en-7-ol or a carboxylic acid ester thereof from a dimethylcyclooctene starting material made up of a mixture of dimethylcyclooctene isomers comprising 1,5-dimethylcyclooctene in admixtue of 1,6-dimethylcyclooctene and/or 1,4-dimethylcyclooctene by the process steps which comprise:
   (a) thermally isomerizing the dimethylcyclooctene isomer mixture to afford a mixed open-chain octadiene product comprising 2,6-dimethylocta-1,7-diene in admixture with 2,7-and/or 2,5-dimethylocta-1,7-diene,
   (b) contacting the mixed octadiene product with a carboxylic acid whereby the 2,6-dimethylocta-1,7-diene selectively reacts to form an ester of 3,7-dimethylocta-1-en-7-ol, and
   (c) optionally hydrolyzing the ester of 3,7-dimethylocta-1-en-7-ol thus formed under basic conditions to yield 3,7-dimethylocta-1-en-7-ol.

2. The process according to claim 1 in which the starting material has been obtained by the selective hydrogenation of a mixture of 1,5-dimethylcycloocta-1,5-diene and 1,6-dimethylcycloocta-1,5-diene in the presence of a noble metal catalyst.

3. The process according to claim 2 in which the thermal isomerization is carried out at 500° to 550° C.

4. The process according to claim 3 in which the carboxylic acid used in step (b) contains up to 4 carbon atoms.

5. A process according to claim 4 in which the step (b) is carried out at 0° to 60° C.

6. A process acccording to claim 1 in which the hydrolysis step (c) is carried out by reacting the ester with an alkali metal hydroxide in an aqueous alkanol.

* * * * *